United States Patent [19]

Smith

[11] Patent Number: 4,491,796

[45] Date of Patent: Jan. 1, 1985

[54] BOREHOLE FRACTURE DETECTION USING MAGNETIC POWDER

[75] Inventor: Dan G. Smith, Houston, Tex.

[73] Assignee: Shell Oil Company, Houston, Tex.

[21] Appl. No.: 359,635

[22] Filed: Mar. 18, 1982

[51] Int. Cl.$^3$ .............................................. G01N 3/26
[52] U.S. Cl. ................................................... 324/346
[58] Field of Search ............................... 324/346, 340

[56] References Cited

U.S. PATENT DOCUMENTS 2,401,280  5/1946  Walstrom ............................ 324/346

*Primary Examiner*—Gerard R. Strecker
*Assistant Examiner*—Walter E. Snow

[57] ABSTRACT

A method for detecting fractures in a formation penetrated by a borehole wherein the fracture is first filled with a magnetic material and the formation then logged with an instrument that responds to the earth's magnetic field. The fracture can be filled with a magnetic material by including it in the drilling mud when the well is drilled and changing the mud system before logging. The logging tool can comprise a simple compass or a magnetometer.

6 Claims, No Drawings

BOREHOLE FRACTURE DETECTION USING MAGNETIC POWDER

BACKGROUND OF THE INVENTION

The present invention relates to borehole logging and particularly to a method for detecting and locating the presence of fractures in a formation penetrated by a borehole. Various acoustic logging systems have been developed in an attempt to detect the presence of fractures in a formation penetrated by a borehole but these methods are not entirely successful. The presence of fractures in a formation can be very important in the petroleum industry in deciding whether a formation is capable of commercial production of hydrocarbons. Fractured formations are difficult to detect since they do not provide a consistent, uniform, or recognizable response in any available electrical, nuclear or acoustic logging device or method that is not routinely produced by conditions or effects not related to the presence of fractures.

One method that has been proposed for detecting fractures is an acoustical mapping method such as described in U.S. Pat. No. 3,369,626. In this patent, an ultrasonic source is triggered to direct a beam of ultrasonic energy radially out to impinge upon the borehole wall and the amplitude of the reflected signal is recorded. The recording is normally done on a cathode ray oscilloscope which is photographed to provide a permanent record of the borehole wall. This method is successful in locating fractures under those conditions in which the fracture is open an amount sufficient to reduce the amplitude of the reflected signals. Another method that has been devised for locating vertical fractures in a formation is that described in U.S. Pat. No. 4,130,816. This patent describes a logging tool in which a transducer admits a burst of sonic energy that is so directed that it produces shear waves in the formation. The shear waves travel around the circumference of the borehole and are received at a receiving transducer. The amplitude of the received shear waves is then recorded to determine the locations of fractures since an open fracture will reduce the amplitude of the received shear wave.

In addition to the above acoustic methods it has also been suggested that a moldable plastic or soft rubber could be pressed against the borehole wall to obtain an impression of the borehole wall that would indicate the presence of fractures. It is obvious that this type of device will only work where the fractures are open and of a substantial width. Since many fractures are small, this method is of limited usefulness in locating formations capable of commercial production.

SUMMARY OF THE INVENTION

The present invention solves the above problems by providing a method for detecting fractures including extremely small fractures. The present method will detect any fractures which are capable of fluid communication with the borehole including their orientation and extent. The method of the present invention comprises the steps of first introducing a magnetic material into the fractures. The material may be injected by suspending it in the drilling mud during the initial drilling of the borehole in which case the material will flow into the freshly exposed fractures before a mudcake is built up on the wall of the borehole. If the material is not introduced in the borehole with the drilling fluid it is necessary to remove the mudcake prior to introducing the material into the fractures. After the magnetic material has been placed in the fractures, the fluid in the borehole is removed and replaced by a nonmagnetic fluid and the borehole logged with a surveying instrument capable of detecting the difference between the earth's normal magnetic field and that caused by the presence of the magnetic material in the fractures. In some cases it may be desirable to introduce a strong magnetic field at 90 degrees to the earth's normal magnetic field and then measure the direction and intensity of the residual magnetic field to detect the presence of fractures. The strength or intensity of this residual field would be proportional to the number and width of any fractures present since more and/or wider fractures would contain more magnetic material and hence have a stronger magnetic field. Further, the orientation of the fractures could be determined from the direction of the magnetic field. This method is not only different from other fracture detection methods in its principle of operation, it is exclusive in that it provides a means to not only detect fractures but determine their direction and extent.

DESCRIPTION OF PREFERRED EMBODIMENTS

As explained above the method of the present invention is carried out by first introducing magnetic material into the fractures in the formation penetrated by the borehole. The magnetic material may comprise finely divided iron, iron powder, nickel or similar magnetic materials or alloys of materials that exhibit magnetic properties. The material should be of a size in the range of 5 to 10 microns to ensure that it penetrates the extremely small fractures. An effective way to introduce the magnetic material into the fractures is to include the material in the drilling mud used in drilling the well. This would allow the material to flow into the fractures as soon as the fractures are exposed by the drilling operation. This would ensure that the material penetrates the fractures prior to the penetration of the fractures by other contaminating fluids or materials contained in the drilling fluid.

In some cases, it may not be desirable to include magnetic material in the drilling fluid, particularly where it is desired to conduct various logging operations in the borehole, particularly electrical surveys. In these cases, it would be necessary to drill the borehole using conventional drilling fluids, conduct the necessary logging operations and then remove the mudcake from the borehole wall by reaming or similar procedures. After the mudcake is removed the magnetic material may be introduced into the fluid in the borehole and forced into the fractures. This, of course, could be accomplished by packing-off or otherwise isolating the formations of interest, introducing the magnetic material into the zone and increasing the pressure in the isolated portion of the formation a sufficient amount to force the magnetic material into the fractures.

After the magnetic material has been injected into the fractures, it is necessary to remove the magnetic material from the fluid in the borehole. This can be accomplished by circulating the drilling fluid or the fluid present in the borehole, out of the borehole while at the same time replacing it with a nonmagnetic fluid. For example, the magnetic fluid may be replaced by conventional drilling fluids which are normally nonmagnetic.

Following the removal of the magnetic fluid from the borehole and its replacement with nonmagnetic fluid, the borehole is logged with an instrument which can detect the distortion or change of the earth's normal magnetic field due to the presence of magnetic materials in the fractures. For example, the logging tools described in U.S. Pat. Nos. 2,425,180 and 4,436,039 may be used. Likewise, any conventional magnetometer type logging tool can be used. It is preferable that a background log be run in an unfractured portion of the borehole in which the magnetic material has not infiltrated any fractures to provide a reference or background measurement of the earth's magnetic field. In some cases, especially where the well is drilled using conventional drilling mud, it would probably be desirable to measure the earth's normal magnetic field in the zone of interest prior to introducing the magnetic material into the fractures. In the absence of an actual measurement in the zone of interest, a similar unfractured formation in another portion of the borehole could be logged to determine the earth's normal magnetic field.

In some cases it may be desirable to introduce a strong magnetic field at 90 degrees to the earth's normal magnetic field prior to logging the formation. The formation can then be logged with a tool that provides a measure of both the direction and intensity of the residual magnetic field. The intensity of the field would be related to the extent of the fracture network while the orientation of the fractures could be inferred from the direction of the residual magnetic field. Knowing both the extent and orientation of the fractures would eliminate much of the uncertainty in fractured formations. This will allow an operator to reach a decision on the production potential of the formation. Since the ability of a fractured formation to produce hydrocarbons, particularly crude oil, is directly related to both the magnitude and the extent of the fractures in the formations, the method of this invention can be used in evaluating the formation. It will be particularly useful in deciding whether the well is to be cased and completed. The method of the present invention would also be useful in locating fractured formations in a borehole which then could be evaluated to decide if it is possible to obtain commercial production from the well.

What is claimed is:

1. A method for locating a fractured formation penetrated by a borehole comprising:
   removing the mudcake from the wall of the borehole;
   introducing a magnetic powder in the range of 5 to 10 microns into the borehole so as to penetrate the fracture;
   removing all magnetic material from the borehole; and
   logging the borehole with an instrument that is responsive to the earth's magnetic field to detect any distortions in the earth's normal magnetic field caused by the magnetic powder in the fracture.

2. The method of claim 1 wherein the region of interest in said borehole is isolated prior to introducing magnetic material into the fractures.

3. The method of claim 2 wherein said isolation means is removed prior to logging the borehole.

4. The method of claim 1 and in addition, inducing a strong magnetic field in the formation at right angles to the earth's magnetic field after introducing magnetic material into the fractures and before logging with an instrument sensitive to the magnitude and direction of the residual magnetic field.

5. The method of claim 1 wherein the magnetic material is iron powder in the range of 5 to 10 microns.

6. The method of claim 1 wherein the magnetic material is powdered nickel in the range of 5 to 10 microns.

* * * * *